United States Patent [19]

Reierson

[11] Patent Number: 5,550,274
[45] Date of Patent: Aug. 27, 1996

[54] IN-SITU PHOSPHATION REAGENT PROCESS

[76] Inventor: Robert L. Reierson, 1 Ruthies Run, Cranbury, N.J. 08512

[21] Appl. No.: 400,077

[22] Filed: Mar. 7, 1995

Related U.S. Application Data

[63] Continuation-in-part of Ser. No. 220,339, Mar. 30, 1994, abandoned.

[51] Int. Cl.$^6$ ........................................... C07F 9/09
[52] U.S. Cl. ................................................. 558/110
[58] Field of Search .............................. 558/110

[56] References Cited

U.S. PATENT DOCUMENTS

| | | | |
|---|---|---|---|
| 3,235,627 | 2/1966 | Mansfield | 260/926 |
| 3,686,371 | 8/1972 | Hasegawa | 260/980 |
| 4,126,650 | 11/1978 | Via et al. | 260/980 |
| 4,139,485 | 2/1979 | Imokawa et al. | 252/135 |
| 4,350,645 | 9/1982 | Kurosaki et al. | 260/978 |
| 4,670,575 | 6/1987 | Kurosaki et al. | 558/146 |
| 4,874,883 | 10/1989 | Uphues et al. | 558/150 |
| 5,254,691 | 10/1993 | Mori et al. | 548/111 |

FOREIGN PATENT DOCUMENTS

| | | |
|---|---|---|
| 42-30167 | 3/1967 | Japan . |
| 3188089 | 8/1991 | Japan . |

OTHER PUBLICATIONS

G. Imokawa, J. Am. Oil Chem. Soc. 56, 604 (1979).
A. Nelson & A. Toy, Inorg. Chem., 2, 775 (1963).
T. Kurosaki et al., Oil Chemistry, 39 (4), 259, (1990).
T. Glonek, et al., J. Am. Chem. Soc. 92, 7214 (1970).
T. Glonek, et al., Inorg. Chem. 13, 2337 (1974).
T. Glonek, et al., Phosphorus 1975, 157.
T. Glonek, et al., J. Am. Chem. Soc. 97, 206 (1975).
T. Glonek, et al., Phosphorus and Sulfur 3, 137 (1977).
M. Watanabe, et al., Mem. Chubu Inst. Tech., 81 (1983).
T. Kurosaki, et al., Comun. Jorn. Com. Esp. Deterg., 19, 191 (1988).
T. Khwaja et al., J. Chem. Soc. (C) 1970, 2092.
T. Kurosaki, et al., Oil Chemistry, 39 (4), 250 (1990).

*Primary Examiner*—Johann Richter
*Assistant Examiner*—Michael G. Ambrose
*Attorney, Agent, or Firm*—John A. Shedden

[57] ABSTRACT

The invention relates to a simple, single-stage process to produce alkyl phosphate esters having high monoalkyl phosphate content in combination with low dialkyl phosphate, trialkyl phosphate, phosphoric acid and other nonionic (usually residual alcohol) components in which a unique phosphation reagent having a preferred effective equivalent polyphosphoric acid concentration of 121–123% is produced and utilized in-situ.

9 Claims, 1 Drawing Sheet

IN-SITU PHOSPHATION REAGENT PROCESS

FIELD OF THE INVENTION

This is a continuation-in-part of U.S. Ser. No. 08/220,339 filed Mar. 30, 1994, now abandoned.

This invention relates to a unique phosphating agent and to a simple, reliable process in which this agent is prepared in-situ to produce phosphate ester compositions which have high monoalkyl phosphate content in combination with low dialkyl phosphate, trialkyl phosphate, phosphoric acid and other nonionic components, such as alcohol starting material.

DESCRIPTION OF THE PRIOR ART

The superior performance of fatty alcohol based anionic phosphate esters enriched in monoalkyl ester content relative to dialkyl content has been demonstrated, particularly with respect to surfactant esters used in cosmetic and personal hygiene cleansers. These high monoalkyl phosphate surfactants exhibit a unique combination of good detergency and low skin irritancy, especially in comparison to alkyl sulfate or alkyl sulfonate surfactants (G. Imokawa, et al., U.S. Pat. No. 4,139,485, G. Imokawa, *J. Am. Oil Chem. Soc.* 56, 604 (1979)). In a given alkyl phosphate mixture, other important properties such as water miscibility, Krafft point and foam production are also a function of the relative amounts of monoalkyl and dialkyl phosphate. As the dialkyl phosphate content increases, the solubility, foaming ability, and detergency decrease and the Krafft point increases. The desirable range for a "monoalkyl" phosphate composition has been defined to be wherein the ratio of monoalkyl to dialkyl phosphate is at least 80:20 weight percent (U.S. Pat. No. 4,139,485). Acceptable performance was found at 70:30, and relatively little additional improvement was obtained above 90:10.

Typical phosphation processes do not produce product mixtures with the high monoalkyl phosphate together with the low dialkyl phosphate, low phosphoric acid and low residual alcohol contents necessary to obtain the above advantages. The two commonly used phosphating agents produce two extremes in the compositional range.

In one case, polyphosphoric acid, commercially available as 115% phosphoric acid (also described as 83 weight percent phosphoric anhydride, $P_4O_{10}$) reacts with alcohols to produce a mixture of moderately high monoalkyl phosphate and low dialkyl phosphate but also high phosphoric acid. This is expected since the polyphosphoric acid consists essentially of linear chains varying from one to more than fifteen phosphorus atoms connected by oxygen anhydride linkages. Although the alcoholysis reaction is complex because it involves many intermediates of differing chain lengths and even cyclic structures, ultimately one molecule of phosphoric acid would theoretically be produced from the "tail-end" of each chain, or alternatively, the amount of phosphorus remaining as $H_3PO_4$ would be equal to $1/\bar{n}$ wherein $\bar{n}$ equals the average polymer chain length (F. Clarke and J. Lyons, *J. Am. Chem. Soc.* 88, 4401 (1966)).

On this premise, the amount of phosphoric acid which would be produced from the chain ends by complete alcoholysis of a sample of an approximately 117% polyphosphoric acid was calculated to be 23.2 mole percent. Reaction of simple alcohols with an equimolar amount of 117% polyphosphoric acid was reported to produce from 21.0 to 23.8% orthophosphoric acid (F. Clarke and J. Lyons, op. cit.). An excess of alcohol was necessary to drive the reaction to completion. Similarly, reaction of an excess of lauryl alcohol with 115% polyphosphoric acid at 70°–83° C. for 15 hours, then to 94° C. for four hours, produced a very viscous oil which solidified upon standing, (m.p. about 80° C.), with no residual pyrophosphates and an orthophosphate composition of 23 mole percent phosphoric acid, 73% monolauryl phosphate and 4% dilauryl phosphate. Expressed as weight percent of total phosphorus products, this would be 9.6% phosphoric acid, 83.0% monolauryl phosphate and 7.4% dilauryl phosphate, to note how the numbers are changed by the molecular weight differences.

To produce a monoalkyl phosphate without dialkyl phosphate contamination theoretically could be done from pyrophosphoric acid (A. Nelson and A. Toy, *Inorg. Chem.*, 2, 775, (1963)). Alcoholysis would yield one mole of phosphoric acid and one mole of monoalkyl phosphate (also F. Clarke and J. Lyons, op. cit.).

Reaction of lauryl alcohol in a molar amount equal to the pyrophosphoric acid plus tripolyphosphoric acid in 105% polyphosphoric acid at room temperature to 65° C. over a two hour period followed by fourteen hours at 71°–72° C. produced a creamy, very viscous mass which contained about 69 mole % phosphoric acid, 20 mole % monolauryl phosphate and 11% pyrophosphate intermediates. Addition of excess alcohol to the mass at room temperature followed by heating to 52° C. over three hours to complete the conversion of the pyrophosphates gave a solution in which the molar ratios were 76% phosphoric acid, almost 24% monolauryl phosphate, and only a trace of dilauryl phosphate. The theoretical distribution based on the original 105% polyphosphoric acid composition was 73% phosphoric acid and 27% lauryl phosphate.

Because of the relatively low reactivity of the pyrophosphate intermediates with the alcohols, an excess of one of the reactants is usually used. U.S. Pat. No. 3,235,627 discloses that an equivalent ratio of 1.2–4.0 polyphosphoric acid per mole alcohol produces a mixture of 85–100% monoalkyl phosphates. In this patent, the optimum ratio per mole alcohol is 1.0 to 1.3 moles polyphosphoric acid, expressed as 82–84% (by weight) $P_2O_5$ (or $P_4O_{10}$; also equivalent to about 115% weight percent polyphosphoric acid). This '627 patent notes however that a large percentage of unreacted alcohol will remain, i.e. incomplete phosphation will occur, if an excess of this polyphosphoric acid is not used. For instance, an equivalent amount (0.5 "mole" expressed as $P_2O_5$ or 0.25 $P_4O_{10}$ per mole alcohol) produced only a 56% conversion; hence 44% residual alcohol. This patent provides references to the art which practice the use of excess alcohol, claiming that undesirable dialkyl phosphates are produced. Additionally, T. Kurosaki et al., *Comun. Jorn. Com. Esp. Deterg.* 19, 191 (1988) states that monoalkyl phosphate can be formed with little formation of dialkyl phosphate, but also that polyphosphoric acid was required in excess to complete the reaction. In the graphical representation of his data, FIG. 14, p. 204, which covers the range of 100 to 115% polyphosphoric acid, he shows that a stoichiometric amount of the most concentrated acid evaluated, about 113%, produces only 60% alcohol conversion and requires a two-fold molar excess to achieve about 95% conversion. He concludes that in order to manufacture high purity monoalkyl phosphate, the removal of the resulting excess phosphoric acid coproduct from the mixture is required.

It is clear that the "polyphosphoric acid" reagents used by this reference were of lower effective equivalent polyphosphoric acid weight percent than that of the reagents of the instant invention which have a minimum of 118 weight percent.

A more recent, comprehensive study of alcohol phosphation by ortho- and polyphosphoric acids similarly shows the limitations of this approach, but considering the value of the high monoalkyl phosphate compositions, commercial processes have been developed based upon 115% polyphosphoric acid alone as the phosphation reagent (T. Kurosaki et al. *Oil Chemistry*, 39(4), 259, (1990)).

The large amount of phosphoric acid thus unavoidably produced in processes based on the common, approximately 115% polyphosphoric acids, is an undesirable coproduct which is particularly troublesome in cosmetic products, electrolyte solutions, emulsions and in the spinning of synthetic fibers. Purification methods have therefore necessarily been developed to partition the acid and the organophosphate into layers which can then be separated (K. Aimono et al. Japan Kokai Tokkyo Koho JP 03,188,089, Aug. 16, 1991; T. Kurosaki et al., U.S. Pat. Nos. 4,670,575, Jun. 2, 1987; G. Uphues et al. 4,874,883, Oct. 17, 1989)).

The other extreme of the product composition is produced by the use of phosphoric anhydride, $P_4O_{10}$. In contrast to 115% polyphosphoric acid, a viscous liquid, $P_4O_{10}$ is a white powder which is highly reactive with alcohols even at room temperature. It is a powerful dehydrating agent and relatively insoluble in most common organic solvents except those with which it reacts. If in excess or not adequately dispersed in the reaction liquor, it forms undesirable by-products, e.g. i) trialkyl phosphates from the primary alcohol and its dialkyl phosphate by dehydration and/or ii) darkly colored products resulting from the charring of the alcohol that was absorbed into the slowly dissolving, large chunks formed by agglomeration of the powder. Under favorable conditions of good mixing and cooling with precise control of adventitious moisture and reactant ratios, the reaction of $P_4O_{10}$ with alcohols still proceeds through a complex series of intermediates. Possible structures for these condensed phosphates have been prepared and characterized (T. Glonek et al., *J. Am. Chem. Soc.* 92, 7214 (1970); *Inorg. Chem.* 13, 2337 (1974); *Phosphorus* 1975, 157; *J. Am. Chem. Soc.* 97, 206 (1975); and *Phosphorus and Sulfur* 3, 137 (1977)). A theoretical sequence is outlined in FIG. 1. The problems with any attempt to control selectivity arise from the fact that each polyphosphate intermediate has its characteristic solubility and reaction rate. Branched phosphates, with three P—O—P bonds to the central phosphorus, are considerably more reactive than linear ones having two P—O—P bonds. The simple pyrophosphate, having only one P—O—P bond, is the least reactive polyphosphate. In addition, hydrolysis studies of the simple acids have shown that the acyclic tetra- and tripolyphosphates are more reactive than their monocyclic precursors, (M. Watanabe et al., *Mem. Chubu Inst. Tech.*, 81 (1983)).

In the presence of other hydroxy functional species such as adventitious water or a mixture of alcohols, the product distribution is a function of the concentration, (which is related to solubility), and the competitive reaction rates of each phosphate intermediate with each hydroxy compound. These conditions change throughout the course of the reaction as the more reactive species are preferentially consumed and their relative concentrations decrease.

The sequence in FIG. 1 predicts that an equimolar mixture of monoalkyl phosphate (MAP) and dialkyl phosphate (DAP) would be formed under ideal conditions and, in fact, reaction of $P_4O_{10}$ with a two fold stoichiometric excess of lauryl alcohol, i.e. 12 moles per $P_4O_{10}$, under standard laboratory conditions produced a mixture of phosphates in a molar ratio of about 0.509 MAP:0.485 DAP:0.007 $H_3PO_4$.

A third option, which is the direct esterification of phosphoric acid, is not practical because of its low reactivity, and the difficulty realized in removing water from the polar and increasingly viscous product mixture. The high temperatures of at least 120° C., reduced pressure of 300 torr or less, preferably less than 50 torr, and/or the use of azeotropic solvents which are used to drive the reaction to completion also produce the undesirable dialkyl phosphates and still leave undesirable levels of unreacted phosphoric acid (T. Kurosaki, et al., *Oil Chemistry*, 39(4), 259, (1990)). Combination of an orthophosphoric acid with an alcohol under less than anhydrous conditions (specifically as 85% orthophosphoric acid) without less than atmospheric pressure, an azeotropic agent or temperatures considerably above the 100° C. water boiling point would not result in an esterification reaction. Similar product compositions may be obtained more conveniently by use of the aforedescribed use of polyphosphoric acid or phosphoric anhydride.

Several attempts to reduce the tendency of phosphoric anhydride to produce dialkyl phosphate coproduct have been reported. Early work postulated that in the optimum case, substitution of two moles of water for two of the six moles of alcohol required to completely convert $P_4O_{10}$ to orthophosphates would produce essentially four moles of the monoalkyl phosphate. (Sanyo Kasei Kogyo K. K., Japanese Patent Publication 41–14416 (1966)). As mentioned above, the reaction sequence is complex. Although high monoalkyl to dialkyl molar ratios of up to 94:6 were reported, substantial conversion of phosphoric anhydride to phosphoric acid also occurred, 60 mole percent, in this example, at the upper end of the "suitable range" of water content, and generally, excessively high levels of phosphoric acid throughout the series. The unreacted alcohol content was not reported, but under the stated conditions of stoichiometry, it could be presumed to be equal to the moles of phosphoric acid minus the moles of dialkyl phosphate or about 58 mole percent. The author clearly stated that the addition of water to the phosphoric anhydride followed by reaction with the alcohol was an unsuitable alternative.

Almost simultaneously, another case (Daiichi Kogyo Seiyaku Co., Ltd., Japanese Patent Publication 42–6730 (1967)) reported the similar use of 85% phosphoric acid (0.960 mole water per mole $H_3PO_4$). This strategy, however, was to react the orthophosphoric acid and the phosphoric anhydride separately with the alcohol apparently in the presence of the water introduced with the 85% phosphoric acid. The details in 94–6730 were limited, but duplication of examples clearly showed that the 85% phosphoric acid did not react with the alcohol under the stated conditions. Complete analysis of the reaction mixtures during and at the completion of the experimental sequence further revealed that the conversion was not complete at the end of the stated reaction period, but rather was finished in the subsequent, apparently necessary work up procedures for separation and characterization of the monoalkyl ester product. Other products were not quantified. The quantities of monoalkyl phosphate found upon duplication of the examples in the laboratory were significantly lower than the high yields of monoalkyl phosphate reported.

A more recent study more precisely determined the affect of the ratios between water, alcohol and phosphoric anhydride on the phosphate product composition, again with particular emphasis upon the monoalkyl and dialkyl phosphate ratio (T. Kurosaki, et al. *Comun. Jorn. Com. Esp. Deterg.* 19, 191 (1988)). High resolution phosphorus-31 nuclear magnetic resonance spectroscopy was used to quantify the phosphorus species during the later stages of the reaction (after the phosphoric anhydride had all dissolved) and in the final mixtures.

The weaker phosphoric acids, 85% and 105% (separated into their percent "water" and "$P_4O_{10}$" content for calculation purposes) were also evaluated. The 105% acid, the lowest concentration of phosphoric acid which is free of residual water (i.e. anhydrous), was found to generally produce less favorable results that the use of water as a diluent in the acid or alone. Even under what appeared to be the most favorable ratios and method, the residual phosphoric acid content was still over 15 mole percent of the total phosphorus species and the monoalkyl phosphate leveled off at about 60 mole percent. The residual alcohol level was not reported.

The use of phosphorus oxychloride is not a good option because it is not selective; it produces three moles of hydrogen chloride per mole of phosphate, which is highly corrosive and must be scrubbed from the reactor emissions to prevent environmental pollution; and it produces an undesirable alkyl chloride by-product (T. Kurosaki et al., U.S. Pat. No. 4,350,645, Sep. 21, 1982).

Even within the limitations of the above phosphation agents, it is possible to obtain desirable intermediate product mixtures by judicious combinations of selected phosphation agents, alcohol and water in staged reaction sequences. For example, the addition of one mole of $P_4O_{10}$ to four moles of an unsaturated alcohol followed by a digestion period, then addition of two moles water and continued heating to completion was reported to yield a high monoalkyl phosphate containing a polymerizable vinyl group for applications in which the presence of any dialkyl phosphate would promote crosslinking of the polymer, and thus be very detrimental (T. Hasegawa, U.S. Pat. No. 3,686,371, Aug. 22, 1972).

A more complicated example involves preparation of a phosphate ester mixture by a standard reaction sequence, and then use of the resulting mixture as the reaction medium to which additional phosphoric anhydride, alcohol, and water are added. The intent is to produce the symmetrical dialkyl pyrophosphate as the major product, then to hydrolyze it to the monoalkyl phosphate in the final step (F. Via et al., U.S. Pat. No. 4,126,650, Nov. 21, 1978).

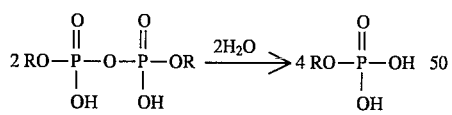

The best results were obtained by multiply staging the reagent addition and heel production events. That is, to the initially formed heel, the remaining phosphoric anhydride and alcohol are alternately added in four equal aliquots at the reaction temperature of 75°–90° C. The mixture is then digested at 85° C. for two hours; water and 30% hydrogen peroxide added; and the reaction completed at 80° C. to yield a final product containing over 80 weight % monoalkyl acid phosphate (based on analysis by titration; phosphorus −31 nuclear magnetic resonance spectroscopy is now more accurate and precise).

The primary study (T. Kurosaki et al., U.S. Pat. No. 4,350,645, Sep. 21, 1982) also utilized a two stage process but in direct opposition to the above two examples. The '371 process, in fact, is very similar to the Method 2 reported to be inferior by this principal author in his 1988 publication (vide supra).

The purpose of the first stage in '645 is to combine an equimolar mixture of water and alcohol with phosphoric anhydride (two moles each, per mole of $P_4O_{10}$) to prepare an intermediate composition, i.e. a heel. This monoalkyl pyrophosphate heel is then reacted with the remaining two

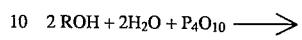

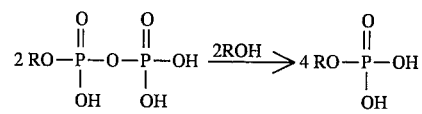

moles of alcohol to convert the pyrophosphate intermediates to orthophosphates. The best product ratios realized for lauryl phosphate, about 0.821:0,081:0.099 MAP:DAP:$H_3PO_4$ (molar) and 0.829:0.134:0.037 (weight) (MAP:DAP weight ratio, 86.1:13.9) for this simplified two step process are comparable to the multiply staged addition process, considering the accuracy of the titrimetric analysis, (U.S. Pat. No. 4,126,650) and are superior to the extant single stage processes. Further specific evidence was provided by Comparative Example 1 in this case. The lauryl alcohol phosphation by 85% phosphoric acid and $P_4O_{10}$ is essentially the same as the Example 1 in 42–6730. The more completely defined composition, however, is reported as 66.2 mole % monoalkyl phosphate, 18.9% dialkyl phosphate and 14.9% phosphoric acid in contrast to the "yield of dodecyl monophosphate: 94.7%" reported in 42–6730.

The above summary essentially describes the state of the existing technology for the preparation of enriched monoalkyl phosphate compositions by direct phosphation and the desirable properties of these compositions, especially for mixtures with MAP:DAP weight ratios of 80:20 or greater. Other, even more sophisticated methods are known which involve the preparation of intermediates in multiple-step processes which have blocking groups that must be removed after the intermediates are used to phosphate the alcohol substrate. The more selective blocking groups would be derived from phenol, substituted phenols, catechol, or substituted triazoles (H. Mori et al., U.S. Pat. No. 5,254,691, Oct. 19, 1993; T. Khwaja et al. *J. Chem. Soc.* (C) 1970, 2092; and the references cited therein). However, these processes are too expensive to be viable for most commercial product applications.

SUMMARY OF THE INVENTION

The present invention relates to the discovery of a unique phosphating agent which, in a single step, solventless process, can be prepared in-situ and used to produce phosphate ester compositions wherein the weight ratio of monoalkyl acid phosphate to dialkyl acid phosphate is greater than 80:20 concomitant with low levels of free phosphoric acid and residual alcohol.

The optimum phosphation reagent composition is from about 121–123% expressed as an effective equivalent percent of polyphosphoric acid. The reagent is prepared in-situ by intimately blending and exclusively reacting phosphoric acid ($H_3PO_4$) dissolved in an organic alcohol (ROH) with phosphoric anhydride ($P_4O_{10}$). This reagent, in the alcohol medium, ultimately reacts with the alcohol to produce the phosphate ester compositions of this invention.

The essence of this in-situ reagent process lies in the discovery that the highly selective phosphation reagent of this invention can be prepared and utilized during a single reaction stage phosphation process by first preparing a solution of phosphoric acid dissolved in organic alcohol(s) under essentially non-reactive temperature conditions; and then intimately blending an appropriate amount of phosphoric anhydride into the acid-alcohol solution with sufficient stirring and temperature control to form the phosphation reagent; and finally, carrying out the phosphation reaction to completion.

The primary phosphate ester products of the present invention have the general formula:

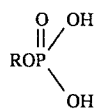

wherein R is as defined herein.

DETAILED DESCRIPTION OF THE INVENTION

Figure 1:
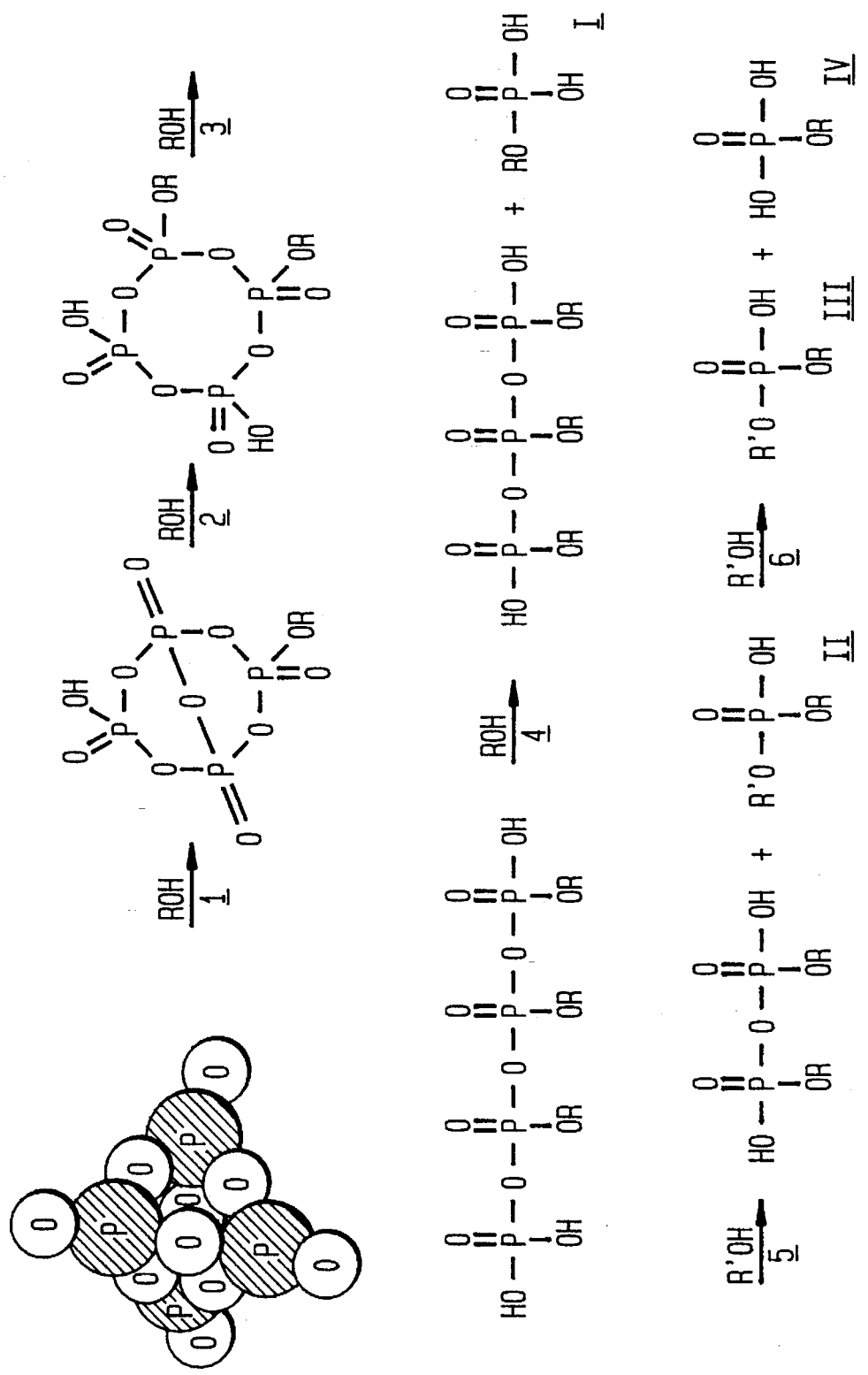
FIG. 1 describes the theoretical step-wise reaction of an alcohol with phosphoric anhydride ($P_4O_{10}$).

A new process has been discovered which produces enriched monoalkyl phosphate ester compositions in a single step which avoids the disadvantages associated with the processes of the prior art. A unique phosphating agent is utilized which is a direct derivative of phosphoric anhydride in which phosphoric acid is used as a blocking group. In the application entitled "Phosphation Reagent and Use" filed concurrently herewith and whose disclosure is incorporated herein, it has been shown that this new reagent may be prepared independently and quantitatively under a wide range of times and temperatures and, when isolated, is stable to storage under anhydrous conditions. It dissolves more readily than phosphoric anhydride, is pumpable when warmed to reduce its viscosity, and can be added more rapidly to the alcohol without the highly exothermic heat of reaction problems characteristic of phosphoric anhydride.

It has now been discovered that this selective phosphation reagent can be prepared and utilized during a single reaction stage phosphation process by first preparing a reactant solution of phosphoric acid dissolved in organic alcohol(s) under essentially non-reactive temperature conditions; and subsequently intimately blending an appropriate amount of phosphoric anhydride into the reactant solution with sufficient stirring and temperature control to form the phosphation reagent. Finally the phosphation reaction between the unique reagent and the alcohol is completed by increasing the temperature of the reagent-alcohol mixture.

Apparently, under appropriate temperature conditions, the phosphoric anhydride reacts with the —OH group of the phosphoric acid preferentially as the anhydride is added to the acid-alcohol solution to form the phosphate group-blocked phosphation reagent which then subsequently reacts with the alcohol in the same manner as the reagent would have reacted had it been prepared in a separate process prior to addition to the alcohol.

In contrast to the use of the commercially available, 115–117% polyphosphoric acids alone, it has been discovered that with the use of this phosphation reagent prepared in-situ, it is not necessary to use an excess of acid relative to the alcohol in order to achieve good conversion rates and low residual alcohol content. In fact, stoichiometrically equal amounts of alcohol and the phosphation reagent are most desirable. The phosphoric acid used as the blocking group is consumed in the process, hence does not contribute excessively to the residual amount. Consequently, the residual phosphoric acid concentration is comparable to that obtained by the most preferable multi-staged processes previously described.

With the process of the instant invention, in which monoalkyl to dialkyl phosphate weight ratios equal to a greater than 80:20 are achieved, the weight percents of the residual alcohol and phosphoric acid are individually each less than 6%.

The action of this reagent is postulated to be as follows, for the simplest case of orthophosphoric acid as the blocking group.

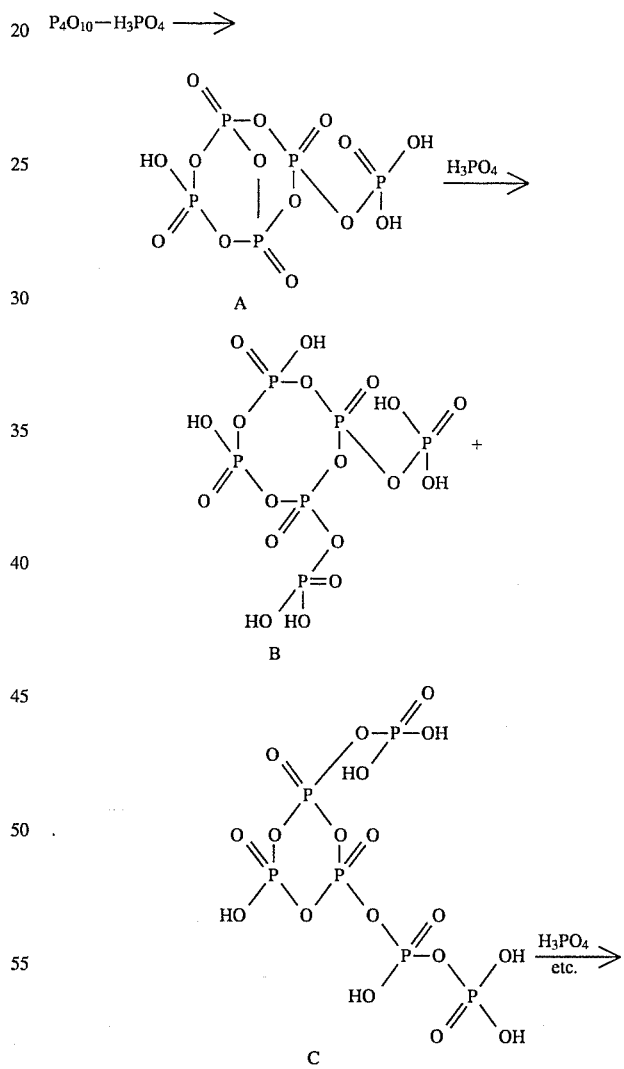

Note that these initial reactions are similar to those already shown in the theoretical $P_4O_{10}$ reactions with alcohol in FIG. 1 in which the R group would represent $H_2PO_3$—. The same principles apply but with important limitations.

The above series of reactions could continue, in the absence of competing reagents, particularly if sufficient phosphoric acid were available, or by further reaction of the —OH functionalities on the blocking phosphate groups, until the more reactive branched phosphates had been converted to linear P—O—P structures. A very complex mixture of intermediates would likely be formed. It is, therefore, important to limit the amount of phosphoric acid to a molar ratio of two per $P_4O_{10}$ molecule (or two phosphorus equivalents of phosphoric acid to the four phosphorus equivalents in $P_4O_{10}$). Substantially more phosphoric acid would convert the reactive, branched intermediates to components comparable to the common, commercially available 115–117% polyphosphoric acids, and substantially less would allow an undesirably high level of the highly reactive tetrahedral $P_4O_{10}$ and its first reaction product, the bicyclic phosphate, to remain. In essence, the latter two highly reactive phosphate species are converted to more controllably reactive intermediates, of which B and C are proposed as examples, and the unreactive (under simple alcohol phosphation conditions) phosphoric acid is converted to more reactive polyphosphate intermediates.

The in-situ generation of these intermediates in an alcohol matrix may place additional constraints on the process. The alcohol may become competitive with the phosphate —OH groups, particularly as the concentration of easily available, unhindered

groups diminishes and reactive species such as the bicyclic phosphate may remain, which, if reacted only with alcohol would contribute to a higher dialkyl phosphate concentration. The presence of the alcohol, therefore, may amplify the sensitivity of the product composition to subtle variations in raw material purity, especially with respect to contamination by traces of moisture, as this would shift the actual hydroxyl-phosphorus reagent ratios and the reagent composition from the theoretically calculated values.

Because of the transient nature of the phosphation reagent intermediates in the heterogenous alcohol matrix, characterization of the initially formed species is very difficult (T. Kurosaki et al., *Oil Chemistry*, 39(4), 250 (1990)). The branched (trisubstituted) phosphorus, even in the non-bicyclic intermediates, would be expected to be of such reactivity that some might be converted to linear, disubstituted polyanhydride chains by reaction with terminal —$OPO_3H_2$ groups in the process of dissolving the sample in an inert solvent for analysis. However, an indication of the nature of the initial composition of this unique phosphation reagent might be obtained from the phosphorus −31 nuclear magnetic resonance spectrum of a similar composition prepared in the absence of alcohol.

For comparison, the principal component in 105 weight % polyphosphoric acid is phosphoric acid itself, 50 mole %, followed by pyrophosphoric acid, 40 mole %, and finally tripolyphosphoric acid, 10 mole % (including the end groups in the pyrophosphoric acid region). A spectrum for 115 weight % polyphosphoric acid still shows some orthophosphoric acid, 8 mole 8 at −0.5 ppm (relative to external 858 phosphoric acid); a more complex pattern at −13 to −14 ppm comprised of pyrophosphoric acid and the phosphates at the ends of the higher molecular weight chains, accounting for 46 mole 8 of the phosphorus species; and a similar pattern at −26 to −29 ppm, for the remaining 46 mole % internal chain phosphate groups. The spectrum of the phosphation reagent of this invention, in contrast, for a composition equivalent to 122.5 weight % phosphoric acid, shows only a trace of orthophosphoric acid; 11 mole 8 chain end and pyrophosphoric acid groups, at −13 to −14 ppm (only one P—O—P anhydride bond on the phosphorus); 878 middle and/or cyclic phosphate groups at −26 to −29 ppm (two P—O—P anhydride bonds on the phosphorus); and 2 mole % branched phosphate groups (three P—O—P anhydride bonds on each phosphorus), at −37 to −39 ppm. Exhaustive interpretation would be difficult because of the wide range of possible structures. However, it is clear that signals characteristic of $P_4O_{10}$ (−60 ppm) and phosphoric acid are essentially absent, signals for branched and pyrophosphates are minimal, and the bulk of the phosphorus species are of the most desired cyclic or linear anhydride type.

The above comments and highly idealized reaction schemes are the inventor's attempt to theoretically explain the unusual and unexpected characteristics and properties of the reagents of this invention and are not meant to limit his discovery; the metes and bounds of which are determined by the scope of the claims.

The composition of the phosphation reagent of this invention is critical and exists within a narrow composition range. The phosphoric acid component used may be in a concentration range of from about 75 to about 117% (about 54 to about 85% $P_4O_{10}$) and is conveniently available commercially in the range of from essentially about 85 to about 115%. The phosphoric anhydride is of high purity and essentially anhydrous.

In the preparation of the acid-alcohol reactant solution, the sequence of addition may be important, depending upon the choice of reagents. The important criterion is that the phosphoric acid component be dissolved in the organic alcohol under essentially non-reactive conditions. Heat can be applied to expedite dissolution of the acid in the alcohol, but preferably, the temperature of the solution should not exceed about 65° C.; more preferably not exceed about 45° C. and that the times at temperatures beyond the preferred range be minimized. For phosphoric acids of about 105% or less, the acid may be added to the alcohol or alcohol to acid within the mixing and temperature constraints of the reactor in accordance with standard practices well known in the art. However, for concentrations above 105%, particularly of about 115%, it becomes more difficult to obtain the desired solution under non-reactive conditions because of the higher reactivity of the polyphosphoric acid and its higher viscosity. Blending the alcohol into the viscous polyphosphoric acid with good mixing and temperature control (avoidance of areas of localized heating on "hot spots") in a timely manner becomes difficult. In this case, therefore, addition of the polyphosphoric acid to the alcohol with appropriate mixing and cooling would be preferred.

The organic hydroxy compounds which can be phosphated by the phosphation reagent of this invention are of the formula $RO\{C_nH_{2n}O\}_xH$ wherein R is selected from the group consisting of a saturated or unsaturated aliphatic $C_1$–$C_{30}$ straight or branched carbon chain, a phenyl, a mono-,di-,or tri-substituted phenyl, a phenyl $C_1$–$C_6$ alkyl and a mono-,di-,or tri-substituted phenyl $C_1$–$C_6$ alkyl, wherein the phenyl substituent group(s) each have a total of 1 to 30 carbon atoms, and wherein each substitution can be a saturated or unsaturated straight or branched carbon chain, a phenyl, an alkyl phenyl, a phenyl alkyl, or an alkyl phenyl alkyl group; wherein n is from 2 to 4 and may be the same or different for each alkylene oxide unit; and wherein x if from 0 to 100.

Examples of the preferred alcohols are lauryl, myristyl, and cetyl alcohols and their ethoxylates, blends thereof; and tristyrylphenol ethoxylates.

In general, an increase in the MAP:DAP ratio occurs as the composition of the in-situ generated phosphation reagent shifts from phosphoric anhydride rich to phosphoric acid rich. A 70:30 MAP:DAP ratio is produced by an independently prepared 125% composition. This is the lower limit of the product mixtures shown to have useful foaming and solubility properties (H. Mori et al. U.S. Pat. No. 5,254,691, Oct. 19, 1993) and considering other process factors such as viscosity and dissolution rates, defines the upper limit of the desirable composition range. The similarly prepared 127% composition results show it to be beyond a desirable composition range.

The MAP:DAP ratio similarly produced by a 119.9% composition is in the favorable range, but the residual phosphoric acid and alcohol levels both increase noticeably. These trends are more pronounced for a 115% composition. Control experiments in which 115% polyphosphoric acid is used directly for the phosphation produce similar results, therefore, the phosphation-reagent composition and process for either this in-situ or separately prepared reagent offers no advantage at that concentration. The upper limit of commercial processes in which polyphosphoric acid is produced by orthophosphoric acid dehydration is about 117.5% because of the excessively high viscosities resulting from the long anhydride polymer chains.

The reagent compositions prepared in accord with this invention contain branched chains and cyclic intermediates. They, therefore, do not suffer from such high viscosity problems either as the reagent itself or in the intermediate alcohol mixtures which they produce in the course of their use. Since the 115% phosphation reagent composition performs as though it were a polyphosphoric acid at the 115% concentration, the reagent would be expected to provide a continuum of compositions with the lower limit of its useful range being that in which use of commercially available polyphosphoric acid becomes impractical, about 117–118%.

Thus, the narrow phosphation reagent composition range is from about 118% to about 125% (expressed as an effective equivalent percent polyphosphoric acid); preferably from about 119%–124% and most preferably from about 121%–123%.

Having determined the appropriate amounts of phosphoric acid and phosphoric anhydride to prepare the phosphation reagent, all that is required is to ensure that the reagent and the organic alcohol are initially present in the proper stoichiometric molar ratio of four alcohols per $P_4O_{10}$ mole equivalent, i.e. equimolar alcohol-phosphorus.

Excess alcohol does not significantly change the MAP:DAP ratio and will contribute to a higher residual alcohol content in the final ester product. Use of significantly less than the stoichiometric amount of alcohol retards the dissolution rate and leaves an undesirably high level of pyrophosphate intermediates which would have to be converted by addition of additional alcohol and/or water.

Since i) it is desirable to minimize alcohol phosphation by the polyphosphoric acid prior to the $P_4O_{10}$ addition, and ii) the reagent formation is an exothermic reaction; the acid-alcohol solution is preferably cooled to below 45° C. prior to the addition of the phosphoric anhydride and kept preferably below about 60° C. during the phosphoric anhydride addition.

As is well known in the art, addition of alcohol to $P_4O_{10}$ powder can result in a vigorous, uncontrollable, potentially hazardous reaction. Therefore, the $P_4O_{10}$ should be added to the acid-alcohol solution and not the other way around.

The temperature of the organic alcohol with the in-situ prepared phosphation reagent admixed is then raised to initiate and complete the phosphation reaction. The times and temperatures required for reacting the phosphation reagent with the alcohol can be easily determined by those skilled in the art and are primarily a function of the mixing, pumping, and temperature control capabilities of the reactor and associated equipment. Reaction temperatures may range from 70° C. to 110° C. Preferably, the temperature range of the reaction should be from about 75° C. to about 100° C.; most preferably from about 79° C. to about 90° C. This cook temperature is essentially dictated by the need to obtain reasonably short reaction times without excessive discoloration of the product.

Typical batch process post-phosphoric anhydride cook times are from greater than 3 to about 12 hours depending upon the reaction temperature. Times from about 4 to about 11 hours are preferred for the preferred temperature range, and from about greater than 4 to about 7 most preferred, to prevent product degradation and color formation.

During the reaction process, a point is reached at which the principal remaining phosphate intermediates are the relatively unreactive pyrophosphates, which together with the alcohol are at low concentration. Since little additional beneficial change in the composition can be achieved by prolonged heating, it is expedient to add a small amount of water to complete the conversion of the pyrophosphates to orthophosphates. Upon completion of this step, the liquor is customarily cooled slightly and hydrogen peroxide is added to reduce the color. The amounts, delivery methods and time of insertion for the above optional additives are known to those skilled in the art and can be determined with minimum experimentation.

The formation of the solution; temporary storage of the solution; in-situ formation of the phosphation reagent; and the phosphation reaction should preferably take place under anhydrous conditions.

The characteristics of the above process for the formation of the phosphation reagent in-situ and its reaction with the alcohol medium to produce a phosphate ester product mixture, suggest that the process would be adaptable to continuous processes, run either concurrently or consecutively. If part of a continuous process, the mixing (dissolution) and reaction (cook) temperatures could be higher because the residence times in the respective zones would be shorter.

The present invention will be explained in more detail with reference to the following non-limiting working examples.

EXAMPLE 1. Lauryl Phosphate

A predried, 12 l flask was fitted with an overhead motor driven Teflon paddle stirrer, thermometer, pressure equalizing addition funnel, inert gas inlet, and outlet through a condenser and silicone oil filled bubbler tube. The system was warmed by mantle and infrared heat lamp under a slow argon gas flow for two hours to remove air moisture, then charged with 7897.5 g lauryl alcohol (n-dodecanol). The liquor temperature equilibrated to 28° C. with all heat sources off. The addition funnel was charged with 115% polyphosphoric acid which was then allowed to run into the stirred alcohol. Gentle heat was applied to prevent freezing and expedite dissolution. Total charge was 2261.1 g. The maximum temperature was 42° C.

The funnel was quickly replaced by a 1 l flask containing 1132.2 g phosphoric anhydride connected to the reaction flask through two standard taper glass joints and a rubber hose. Air moisture was excluded by a positive flow of dry argon gas during the operation.

The stirred solution was cooled to 32° C. The phosphoric anhydride was sifted into the solution with sufficiently rapid stirring to produce a white, easily stirred slurry. The temperature rose to 55° over the 70 minute addition period and an additional 4° C., to level out at 59° C. over the next 40 minutes. Correction for the 2.5 g flask residue gave a charge of 1129.7 g. This was slightly in excess of the planned charge, so an additional 4.0 g of 115% phosphoric acid and 26.5 g lauryl alcohol were added. Final reagent charges were 42.52 mole lauryl alcohol, 26.58 mole phosphorus from the polyphosphoric acid and 3.98 mole phosphoric anhydride (15.92 mole phosphorus). The average phosphation reagent composition was 122.7% expressed as polyphosphoric acid and the molar ratio of alcohol to phosphorus was 1.0006.

The slurry was heated to 82° C. and maintained at 85°–±3° C. for 11 hours. The resulting pale yellow, clear solution was then cooled to 65° C., and 23.3 g 35% hydrogen peroxide was added to produce a water-white liquid, which was bottled while warm. Analysis by conventional wet and phosphorus-31 nuclear magnetic resonance spectroscopy methods showed the phosphate molar ratios to be 0.126 phosphoric acid, 0.786 monolauryl phosphate and 0.088 dilauryl phosphate. The weight percent nonionics was 0.4 and the phosphoric acid and the phosphates 4.7%, 80.2%, and 14.7%, respectively, resulting in a MAP:DAP weight ratio of 84.5:15.5.

EXAMPLE 2. Lauryl Phosphate

The same apparatus as in Example 1 was assembled, dried and charged with 6996.5 (37.547 mole) lauryl alcohol. The 115% polyphosphoric acid was warmed in the addition funnel by an infrared heat lamp to reduce its viscosity and reduce its addition time. The liquor reached a maximum of 62° C. within 30 minutes after the addition of the 2003.1 g (23.508 moles phosphorus) of polyphosphoric acid and the solution became clear. It was then quickly cooled to 31° C. Phosphoric anhydride was sifted from a 1l flask (which had been charged under argon and attached quickly to the reaction flask neck, under positive argon gas flow, through a rubber hose connection) into the stirred liquor over a 195 minute period during which the temperature reached 56° C.; total charge by difference was 1004.8 g (3.5395 mole; 14.158 moles phosphorus). The ratio of moles alcohol to phosphorus was 0.9968:1.0000. The calculated average composition of the phosphation reagent was 122.7% $H_3PO_4$.

The easily stirred slurry was heated to 81°±1° C. and maintained for seven hours, then allowed to cool overnight. The white solid was remelted at about 51° C., heated to 80° C., and 31.0 g deionized water was added. Heating and stirring were maintained for two hours. The clear, pale yellow liquor cooled to 63° C. and bleached with 20.0 g 35% hydrogen peroxide. The liquor was heated for transfer because the crystals began freezing out at about 61° C.

The nonionic component was only 0.8 weight percent. The phosphate molar ratios were 0.119 phosphoric acid, 0.794 monolauryl phosphate and 0.087 dilauryl phosphate. Weight composition was 4.4%, 80.4% and 14.4%, respectively, with a MAP:DAP ratio of 84.8:15.2.

Comparative Example 1. Two Step Process

Reaction of Lauryl Alcohol with Polyphosphoric Acid

Prior to Phosphoric Anhydride Addition

In a 1l flask equipped similarly to Example 1, 81.1 g 105% phosphoric acid (0.430 mole phosphoric acid, 0.179 mole pyrophosphoric acid and 0.027 mole tripolyphosphoric acid) and 37.0 g dodecyl (lauryl) alcohol (0.20 mole) were combined at room temperature. The temperature of the stirred solution rose to a maximum of 35° C. in 10 minutes and the mixture changed to a whipped cream consistency. It was stiff enough to retain its shape if stirring were stopped, yet was easily stirrable. Heat was applied to raise the temperature to 72° C. within two hours and held for an additional 14 hours. The phosphate composition by $^{31}$P NMR analysis of the viscous, creamy mass was 0.600 mole phosphoric acid, 0.179 mole monolauryl phosphate, and 0.045 mole pyrophosphoric acid, verifying substantial conversion of the polyphosphoric acid components and absence of dialkyl phosphate.

To the 98.0 g which remained after sampling (83.0% of the above mixture), 302.6 g of lauryl alcohol (1.624 mole) was added and the liquor heated to 52° C. to dissolve the phosphate mixture heel. The solution thus containing phosphoric acid and the alcohol phosphate was cooled to 30° C. and 74.9 g phosphoric anhydride was added in nearly equal portions, 25 minutes apart. The powder dispersed readily to produce a white, creamy, easily stirrable slurry with the temperature rising from 41° C. at the end of the addition to a maximum of 61° C. 10 minutes later. The temperature was raised to 80° C. and maintained for 18 hours, 2.4 g deionized water was added, the mixture stirred at 80° C. for two hours, cooled to 60° C. and bottled.

The total raw materials charged were 1.788 mole lauryl alcohol (0.164 mole in heel, 1.624 in step two), 0.719 mole phosphorus (as 105% polyphosphoric acid), and 0.264 mole phosphoric anhydride (1.055 mole phosphorus). The calculated phosphation reagent average composition was 122.7% polyphosphoric acid, and the molar ratio of alcohol to phosphorus was 1.008:1.000. The product phosphate molar ratios were 0.146 phosphoric acid, 0.730 monolauryl phosphate and 0.124 dilauryl phosphate. The weight composition was 1.0% nonionics, 5.4% phosphoric acid, 73.3% lauryl phosphate and 20.3% dilauryl phosphate, with a MAP:DAP ratio of 78.3:21.7. This composition is below the 80:20 ratio regarded as the minimum for a desirable monoalkyl phosphate composition and further below the 85:15 ratio obtained by the process modification of this invention, even though the amount of lauryl phosphate produced in the first step consumed only about 10% of the total alcohol and phosphation reagent charge and contained no dialkyl phosphate coproduct.

The process of the instant invention is decidedly superior to the published Comparative Example 1. in U.S. Pat. No. 4,350,645, in which the phosphoric anhydride apparently was not added entirely under controlled, lower temperature conditions to minimize direct reaction between the phosphoric anhydride and alcohol. The high amount of dialkyl phosphate characteristic of that reaction is reflected in the final product molar composition, which was 0.149 phosphoric acid, 0.662 monolauryl phosphate and 0.189 dilauryl phosphate (conversion of MAP:DAP molar ratio to weight ratio gives 68.2:31.8) even though the overall reagent ratios are an average composition of 122.5% polyphosphoric acid equivalent for the phosphation reagent and the alcohol to phosphorus molar ratio is 1.00:1.00.

Comparative Examples 2 and 3

The following experiments were conducted with regard to Japanese Patent Publication 42–6730.

Comparative to Example 1 of 42–6730

To a predried assembly consisting of a 500 ml round bottomed flask equipped as in Example 1 of this application was charged 186.31 g dodecyl alcohol against a positive flow of argon gas. Phosphoric acid, 85%, was charged to the pressure equalizing addition funnel and 23.40 g was added to the stirred, preheated alcohol over an 11 minute period with the temperature being maintained at 42°–44° C. The liquor temperature was allowed to drop naturally to 38° C. over seven minutes and maintained at 35°–38° C. for two hours with continued stirring. The liquid addition funnel was replaced by an airtight, screw-feed, pressure equalizing powder addition funnel containing phosphoric anhydride during this period. A water bath was raised to the flask and 56.72 g phosphoric anhydride was added with stirring over a 131 minute interval with the temperature at 38°–39° C. The liquor temperature was raised to 60° C. in 35 minutes and maintained at 63°–64° C. for most of the three hour post addition cook period. The liquor was allowed to cool to 58° C. during a four minute period during which a 22.18 g sample was removed.

The liquor was then diluted with 224.54 g anhydrous ethanol and transferred quantitatively to a 3000 ml flask with five washings of anhydrous ethanol; total ethanol diluent weight was 1215.23 g. The solution was heated to reflux in accord with the work up procedure described in the body of 42–6730. A portion of the solution was removed and the ethanol removed under vacuum.

Analysis of the first sample, taken after completion of the process claimed in 42–6730, by quantitative C-13 nuclear magnetic resonance showed the integral ratio between the residual alcohol and the combined alkyl phosphate alpha-carbon signals to be 7.3:92.7, the total integral of these groups matching the value for the terminal methyl group and well resolved individual, internal methylene signals. The P-31 nuclear magnetic resonance spectrum showed the mixture to still contain 13.8 mole percent pyrophosphate intermediates. In view of the 7.3 mole percent unreacted alcohol, and the 13.8 mole percent residual pyrophosphates, it would be impossible to achieve the 94.7% yield of monododecyl phosphate ester as reported by the Japanese Patent Publication 42–6730 without further reaction.

Analysis of the mixture concentrated after the ethanol work-up showed the amount of pyrophosphate intermediates to have been reduced to about 6.8 mole percent; with an approximately even split between the alkyl and non-alkylated groups. The monoalkyl and dialkyl orthophosphate signal regions now both contained overlapping signals, indicating the formation of ethyl as well as dodecyl substituted phosphates; i.e., some of the dialkyl phosphates could contain both an ethyl and dodecyl group and monoethyl phosphate was produced.

The C-13 spectrum similarly confirmed formation of ethyl phosphate species, but at an approximately 12:88 mole ratio to the dodecyl phosphate signals. This ratio of about double that expected from reaction with the portion of the pyrophosphates which were consumed, was explained by the 5 mole percent increase observed in the residual dodecyl alcohol, to 12.3%. Apparently, a small amount of transesterification had occurred.

In a separate experiment, the absence of alkyl phosphates in the dodecyl alcohol –85% phosphoric acid solution after the first "reaction" period (i.e. only orthophosphoric acid was present) was confirmed. Additionally, the two portions of the product mixture purified by separation of the precipitated product from the ethanol soluble product were analyzed. The P-31 spectrum of the filter cake showed molar ratios of 8.6% phosphoric acid, 53.5% monoalkyl phosphates and 37.9% dialkyl phosphates. The solid obtained by evaporation of the ethanol from the filtrate was 15.5% phosphoric acid, 77.5% monoalkyl phosphates and 7.0% dialkyl phosphates. An efficient separation was therefore not achieved in the purification step; monododecyl phosphate was removed in the filter cake and didodecyl phosphate was carried over into the ethanol solution.

Comparative to Example 2 of 42–6730

To a 500 ml flask equipped as in the above comparative example, was added 195.06 g 2-ethylhexyl alcohol under argon. The liquor was warmed to 70° C. and the addition of 85% phosphoric acid was initiated. After 18 minutes, the addition was stopped, for a total of 28.88 g, with the temperature having risen to 73° C. Samples of 10.09 g and 9.74 g were removed after 12 and 77 minutes, the temperature being maintained at 72°–73° C. The P-31 NMR spectrum confirmed that only phosphoric acid was present in both cases; no reaction with alcohol to form esters had occurred.

The solution was cooled to 41° C. and, correcting for the mass removed as samples, 96.73 g phosphoric anhydride was added over a 98 minute period during which the temperature was allowed to rise gradually to 47° C. The reaction was continued at the "same temperature" for 30 minutes, as stated in the 42–6730 example (actually, the temperature rose to 48° C.). Since the mixture was still cloudy with some clumps of phosphoric anhydride remaining, 25.55 g was removed for analysis. The molar ratios of the signals in the orthophosphate (ca. −1 ppm) to pyrophosphate (ca. −13 ppm) to higher polyphosphate (ca. −27 ppm) regions were 23.7: 64.7: 11.6, indicating limited conversion. The liquor was, therefore, heated over the next hour to 70° C. to begin a second 30 minute reaction period at 70°–79° C., assuming "same temperature" meant that which as was used for the phosphoric acid "reaction" period. Analysis of a fresh 25.87 g sample of the mixture after this period showed the ratios between signals in the orthophosphate, pyrophosphate and polyphosphate regions to be 40.4:55.4:4.2, still indicative of very incomplete conversion.

The remaining liquor was diluted with 230.60 g anhydrous ethanol and washed into a 2000 ml flask with three volumes of fresh ethanol for a total of 1251.03 g diluent. The solution was then heated to reflux, heating continued for 20 minutes, then the liquor was allowed to cool naturally in the oil bath and sampled. The clear solution was refrigerated at +10° C. and checked periodically for crystal formation. None was observed over a seven day period, so the work-up was discontinued.

The P-31 spectrum of the final sampled after concentration, showed it to still contain a significant proportion of pyrophosphate intermediates in molar ratio of 32.0:68.0 to the orthophosphates. The pyrophosphate six-signal pattern was essentially the same as that observed from the sample taken prior to the ethanol treatment indicating the only significant change had been conversion of a portion of the pyrophosphates to orthophosphates. The two orthophosphate ester peaks (mono and dialkyl) now both had smaller side peaks showing the presence of the ethyl as well as the 2-ethylhexyl groups of each product.

The C-13 NMR spectrum confirmed the formation of the ethyl substituted as well as 2-ethylhexyl substituted mono- and dialkyl phosphates. The mole ratio of ethyl to 2-ethylhexyl phosphate groups was 21:79.

Although the amount of the various phosphorus species would be difficult to calculate from the final spectra because of the overlap of the ethyl and 2-ethylhexyl signals, an estimate of a final composition which would have been produced from the pre-ethanol treated mixture can be calculated if one made the reasonable assumptions that the pyro and tripolyphosphate intermediates were converted to orthophosphates only by reaction with 2-ethylhexyl alcohol and no significant transesterification occurred. (In this example, such complete conversion would not have occurred because the phosphation reagent was in excess!). The mole percentages of the thus estimated composition would be 12.6% phosphoric acid, 63.9% mono(2-ethylhexyl) phosphate and 23.6% di(2-ethylhexyl) phosphate. Conversion to normalized weight percentages (values would be lower if residual alcohol were present) would be 5.5 weight percent phosphoric acid, 60.3 weight percent mono- (2-ethylhexyl) phosphate and 34.2% di(2-ethylhexyl) phosphate. The calculated MAP:DAP weight ratio would be 63.9:36.1.

The above data show that the claimed procedure was not sufficient to complete the conversion of either the alcohol or phosphorus reagents to orthophosphates. No formation of alkyl phosphates occurred in the first stage reaction of 85% phosphoric acid with the alcohol and completion of the reaction after the phosphoric anhydride addition required the work up procedure involving dissolution in a large excess of ethanol and yet another, additional, undefined heating period to complete the conversion.

In both examples, the product mixtures before and even after the second stage reaction with ethanol, produced mixtures containing such high levels of residual starting alcohol, residual phosphoric acid and/or dialkyl phosphate that the 94.7 and 90.2% yields of monoalkyl phosphate reported were not present at anytime during the process.

Finally, the second example using a phosphation reagent composition effectively equivalent to 125.9 weight percent polyphosphoric acid, approaching the upper end of the 91.4 to 126.8% range described in the 42–6730 case was beyond the 125% maximum useful concentration defined herein and, as expected, produced a weight ratio lower than the 70:30 monoalkyl dialkyl phosphate defined as functionally, but marginally acceptable in performance (See Examples 12 and 13 in appended Table 1 of copending continuation-in-part filed Mar. 6, 1995 of U.S. Ser. No. 08/220,069 filed Mar. 30, 1994.) and certainly lower than the preferred 80:20 ratios produced in the present invention.

Having set forth the general nature and some examples of the present invention, the embodiments in which an exclusive property or privilege is claimed are defined as follows:

1. A process for the production of monoalkyl phosphoric acid ester compositions wherein the monoalkyl to dialkyl phosphate weight ratio is greater than 80:20 and the weight percent of the residual alcohol and phosphoric acid are individually each less than 6% comprising the steps of:

A) preparing a phosphoric acid-alcohol reactant solution by
  i) dissolving
    a) from about 75 weight % to about 117 weight % phosphoric acid in
    b) at least one alcohol medium of the formula $RO\{C_nH_{2n}O\}_xH$, wherein R is selected from the group consisting of a saturated or unsaturated aliphatic $C_1$–$C_{30}$ straight or branched carbon chain, a phenyl, a mono-,di-or tri-substituted phenyl, a phenyl $C_1$–$C_6$ alkyl and a mono-,di-,or tri-substituted phenyl $C_1$–$C_6$ alkyl, wherein the phenyl substituent group(s) each have a total of 1 to 30 carbon atoms, and wherein each substitution may be a saturated or unsaturated straight or branched carbon chain, a phenyl, an alkyl phenyl, a phenyl alkyl, or an alkyl phenyl alkyl group; wherein n is from 2 to 4 and may be the same or different for each alkylene oxide unit; and wherein x is from 0 to 100, under essentially non-reactive temperature conditions;

B)
  i) intimately blending into said reactant solution and
  ii) reacting exclusively the phosphoric acid in said reactant solution with a stoichiometrically effective amount of phosphoric anhydride to produce in-situ a phosphation reagent having an effective equivalent polyphosphoric acid weight percent of from about 118 to 125; and C) reacting the phosphation reagent so produced with the alcohol medium at from about 75° C. to about 100° C. for a reaction time of from about 4 to about 12 hours.

2. The process of claim 1 wherein
  i) the temperature at which the phosphoric acid is dissolved in the alcohol does not exceed 65° C.; and
  ii) the temperature at which the phosphoric anhydride is blended and reacted with the phosphoric acid in the alcohol medium does not exceed 60° C.

3. The process of claim 2 where the phosphation reagent has an effective equivalent polyphosphoric acid weight percent of from about 119 to 124.

4. The process of claim 2 wherein the phosphation reagent has an effective equivalent polyphosphoric acid weight percent of from about 121 to 123.

5. The process of claim 2 wherein the phosphation reaction time is from about 4 to about 11 hours.

6. The process of claim 2 wherein an effective amount of water is added to the phosphation reaction to hydrolyze residual pyrophosphate intermediates.

7. A process for the production of monoalkyl phosphoric acid ester compositions wherein the monoalkyl to dialkyl phosphate weight ratio is greater than 80:20 and the weight percent of the residual alcohol and phosphoric acid are individually each less than 6% comprising the steps of:

A) preparing a phosphoric acid-alcohol reactant solution by
  i) dissolving at 65° C. or less
    a) from about 85 weight % to about 115 weight % phosphoric acid in
    b) at least one alcohol medium of the formula $RO\{C_nH_{2n}O\}_xH$ wherein R is selected from the group consisting of a saturated or unsaturated aliphatic $C_1$–$C_{30}$ straight or branched carbon chain, a phenyl, a mono-,di-,or tri-substituted phenyl, a phenyl $C_1$–$C_6$ alkyl and a mono-,di-,or tri-substituted phenyl $C_1$–$C_6$ alkyl, wherein the phenyl substituent group(s) each have a total of 1 to 30 carbon atoms, and wherein each substitution may be a saturated or unsaturated straight or branched carbon chain, a phenyl, an alkyl phenyl, a phenyl alkyl, or an alkyl phenyl alkyl group; wherein n is from 2 to 4 and may be the same or different for each alkylene oxide unit; and wherein x is from 0 to 100

B)
  i) intimately blending into said reactant solution and
  ii) reacting the phosphoric acid in said reactant solution at 60° C. or less with a stoichiometrically effective amount of phosphoric anhydride to produce in-situ a phosphation reagent having an effective equivalent polyphosphoric acid weight percent of from about 119 to 124; and C) reacting the phosphation reagent so produced with the alcohol medium at from about 79° C. to about 85° C. from about 4 to about 12 hours.

8. The process of claim 7 wherein the phosphation reagent has an effective equivalent polyphosphoric acid weight percent of from about 121 to 123.

9. The process of claim 7 wherein the alcohol is a tristyrylphenol ethoxylate.

* * * * *